United States Patent [19]
Swan et al.

[11] 4,256,098
[45] Mar. 17, 1981

[54] SAFETY RESTRAINT SYSTEM FOR AMBULATORY PATIENTS

[76] Inventors: Algernon G. Swan, 114 Rivershire La., Lincolnshire, Ill. 60015; Eugene A. Stead, Jr., Rte. 1, Box 135, Clarksville, Va. 23927; William P. Thompson, 6315 Scatterfield Rd., Anderson, Ind. 46015; David P. Colvin, Rte. 5, Box 67, Apex, N.C. 27502

[21] Appl. No.: 92,568

[22] Filed: Nov. 8, 1979

[51] Int. Cl.[3] ............................................. A61F 13/00
[52] U.S. Cl. ................................ 128/133; 128/25 R; 5/81 B; 272/70
[58] Field of Search ................ 128/133, 25 R; 5/81 R, 5/81 B, 83, 87-89; 272/70; 104/89

[56] References Cited

U.S. PATENT DOCUMENTS

| | | | |
|---|---|---|---|
| 3,351,959 | 11/1967 | Turpin | 5/89 X |
| 3,721,436 | 3/1973 | Barthel, Jr. | 128/25 R X |
| 3,780,663 | 12/1973 | Pettit | 128/25 R X |

*Primary Examiner*—John D. Yasko
*Attorney, Agent, or Firm*—Shlesinger, Fitzsimmons & Shlesinger

[57] ABSTRACT

This restraint mechanism utilizes a flexible tether or cord, which is attachable at one end to a harness or garment worn by a patient, or the like, and which is attached at its opposite end to an inertial reel. The reel may be mounted for travel in a track or groove formed in a ceiling of a room or the like, or it may be fixed to the ceiling, or even to an overhead frame on a walker. A spring in the reel normally tends to retract the tether to maintain slight tension therein when it is attached to the patient's harness. If the patient should suddenly fall, a centrifugally or hydraulically operated safety mechanism in the reel immediately resists rotation of the reel in an unwinding direction, thereby causing the patient to be lowered gently to the floor. Also, should the tether suddenly be released from the patient's harness, the reel includes a centrifugally or hydraulically operated mechanism for preventing sudden retraction of the tether into the reel. The harness itself may be a garment worn by the patient, or may comprise a plurality of straps wrapped around the patient, and attached by releasable clamps to the lower end of the tether, or to a yoke member attached to the lower end of the tether. The garment or straps may have "Velcro" type closures for releasably securing surfaces thereof together.

14 Claims, 11 Drawing Figures

SAFETY RESTRAINT SYSTEM FOR AMBULATORY PATIENTS

This invention relates to a system designed specifically to prevent falls and consequent injury to individuals that are physically handicapped, confused, disoriented, sedated or otherwise debilitated. More specifically, this invention relates to apparatus for assisting ambulatory patients in walking, and for preventing harm due to any accidental falls of the patients while walking.

Of the numerous accidents which occur each year in hospitals, nursing care institutions, retirement and residential homes, many are the result of accidental falls by the elderly. These falls often result in broken hips or other physical injuries which not only require considerable additional medical care and large hospital and medical expenses, but also cause much unnecessary human suffering. These accidents and resultant injuries add to the total health care costs and ultimately to the increased cost of health care insurance. In well adjusted older people a broken hip often initiates a depressing "beginning-of-the-end" phenomenon from which full recovery is never accomplished.

The most sensible and reasonable solution to this problem is to prevent the injuries to begin with. In the hereinafter described invention, this preventative apparatus comprises, in essence, (1) a restraint member or support garment (2) a tether for attaching the garment to a variable rate inertial reel, and, if desired, (3) an overhead monorail system with (4) switching arrangements to allow the patient to effect movement of the reel and associated safety mechanism from one terminal location in a hospital, or the like, to another (e.g., from bed to bathroom and return, from bed to chair and return, etc.). In somecases, of course, it may be desirable to have the inertial reel fixed to the ceiling or to an overhead frame on a walker, or the like, rather than being mounted for movement along the overhead rail.

The restraint garment may be made from a washable, reusable material, which may double as a sleeping or undergarment, and which has the necessary reinforced portions in the shoulder, underarm and crotch areas to provide "hook-on" or attachment surfaces for connecting the patient to the overhead safety device. The design of the garment, however, depends upon the build of the individual to whom it is to be secured, as well as the nature of the individual's illness. For example, when the sphincters are continent, or when the garment is to be in place for only a few hours, the anchoring areas may be located in the crotch or around the pelvis. When rectal or bladder incontinency is a problem, the garment will be designed to have the anchor areas located in the area of the chest and axilla. Obviously at times both pelvic, chest and axillary anchoring areas can be employed.

It is an object of this invention to provide an improved restraint system and apparatus therefor which is readily attachable to an ambulatory patient, and which restrains the patient from accidentally falling and injuring himself or herself while walking or arising from a bed or the like.

Still another object of this invention is to provide safety apparatus of the type described which is suspended from an overhead monorail or track which enables the harnessed or restrained patient to move about safely without the likelihood of injury from accidental falls, or the like.

Another object of this invention is to provide for use with this novel apparatus an improved harness or restraint garment, which is readily attachable to a patient, and which in turn is adapated to be attached to an overhead safety device to prevent accidental falling of the patient during use.

A more specific object of this invention is to provide safety apparatus of the type described which utilizes an internal reel which is tethered to a garment or harness which is worn by a patient, and which automatically brakes and functions to prevent the patient from falling too fast, whenever the downward movement of the harness and patient exceeds a predetermined rate.

Still another object of this invention is to provide for use with this safety apparatus a novel inertial reel having a centrifugally operated mechanism for braking the reel's rotation when it unwinds in excess of a predetermined rate.

It is an object also of this invention to provide for this safety apparatus a novel inertial reel which has a hydraulically operated mechanism for braking the reel's rotation when it unwinds in excess of a predetermined rate.

Other objects of the invention will be apparent hereinafter from the specification and from the recital of the appended claims, particularly when read in conjunction with the accompanying drawings.

In the drawings:

FIG. 1 is a perspective view of safety apparatus made according to one embodiment of this invention, and showing one form of a patient-supporting harness suspended by a retractable tether from the ceiling of a hospital room or the like;

Figure 4C:
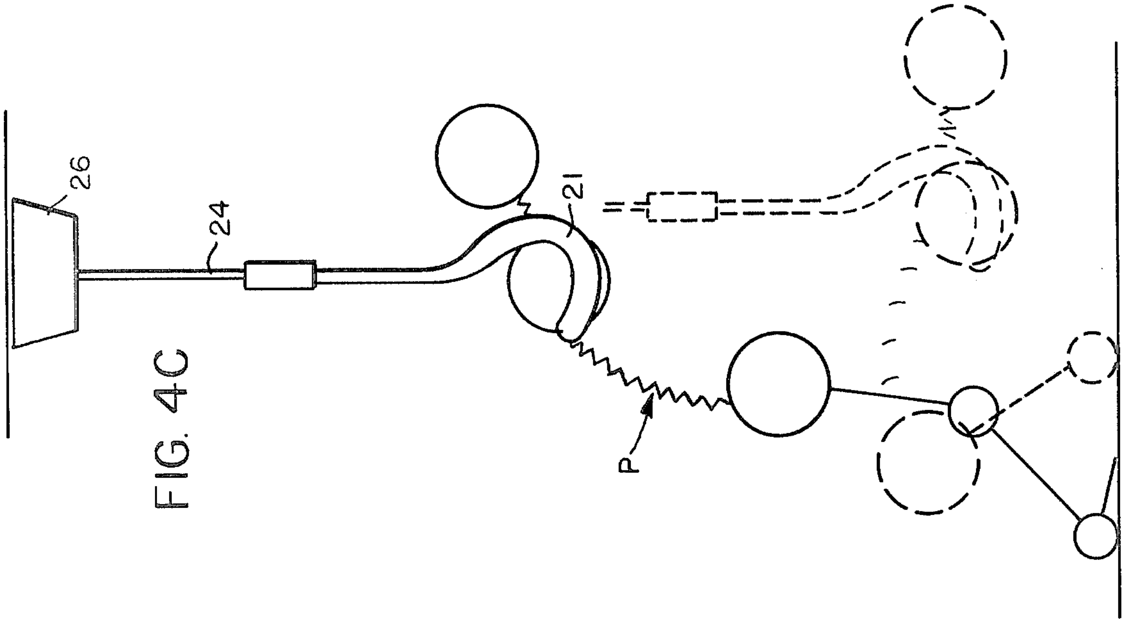
Figure 4B:
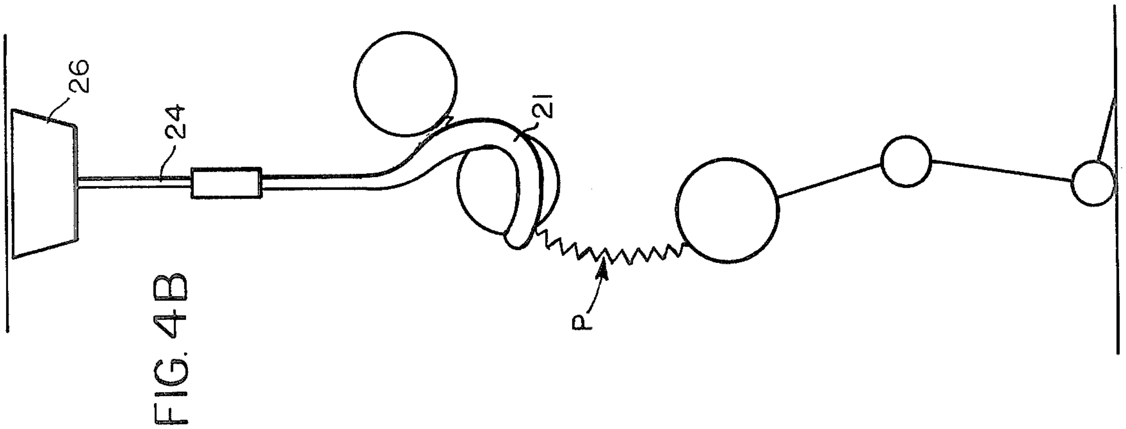
Figure 4A:
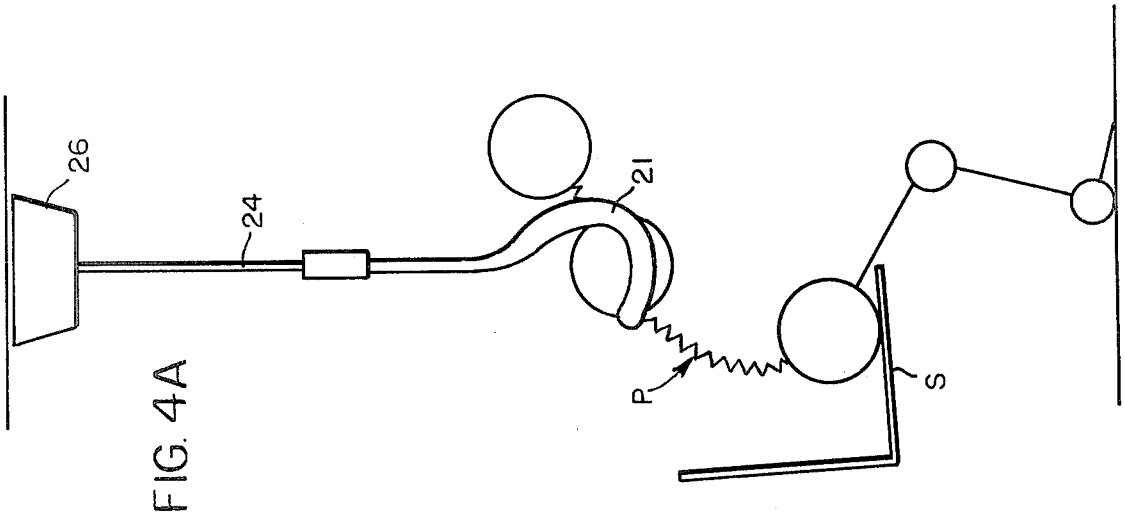

FIGS. 4A, 4B, and 4C illustrate diagramatically the manner in which the safety harness mechanism of this invention is designed to support a human body in sitting, standing and falling modes, respectively.

Figure 2:
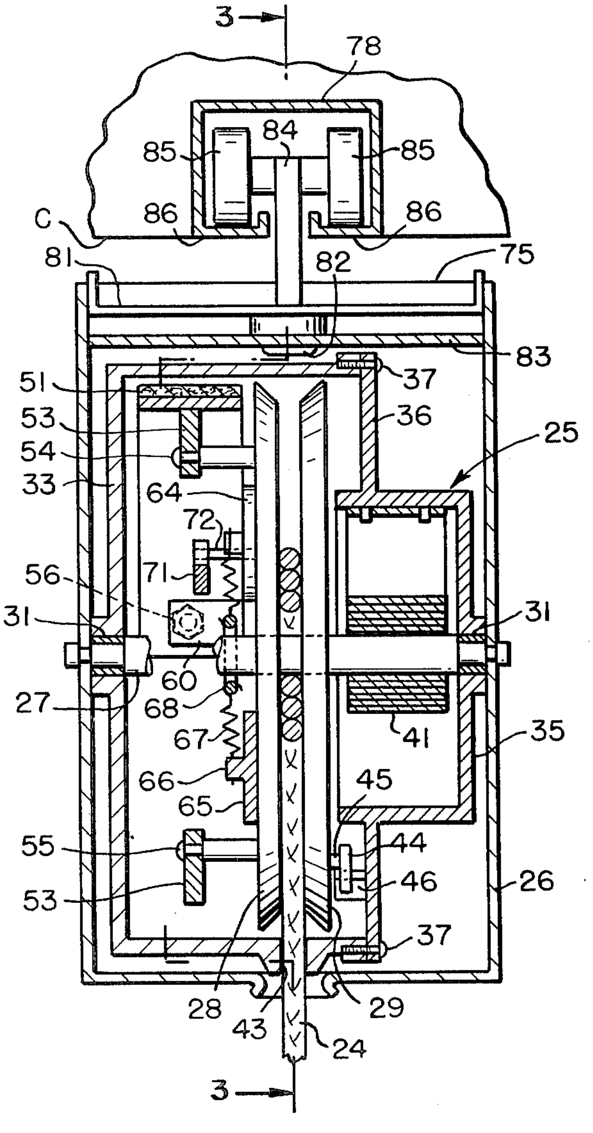
FIG. 2 is an enlarged, fragmentary sectional view taken generally along the line 2—2 in FIG. 1 looking in the direction of the arrows, and illustrating one type of inertial reel which may be employed in this invention.
Figure 5:
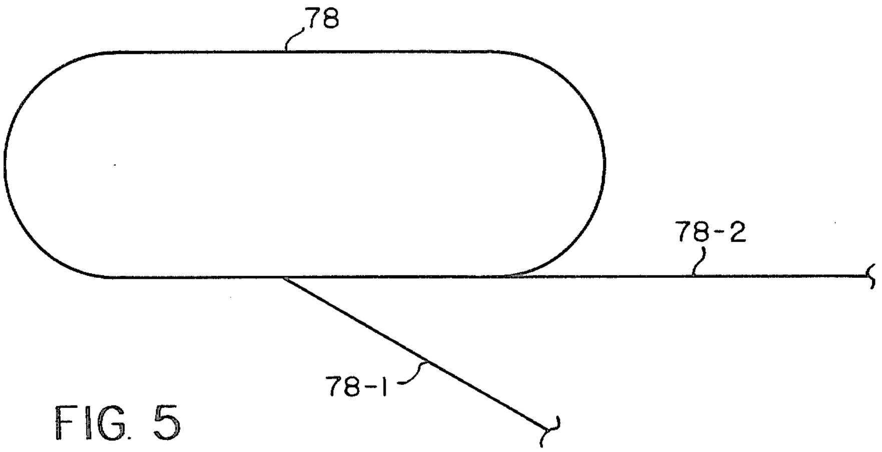
Figure 6:
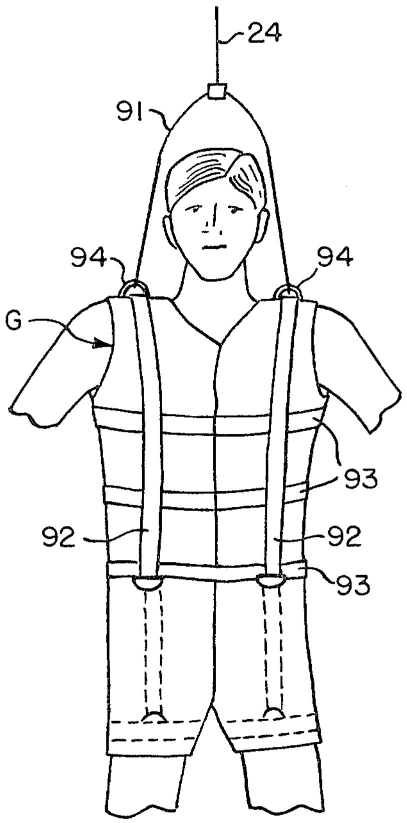
Figure 7:
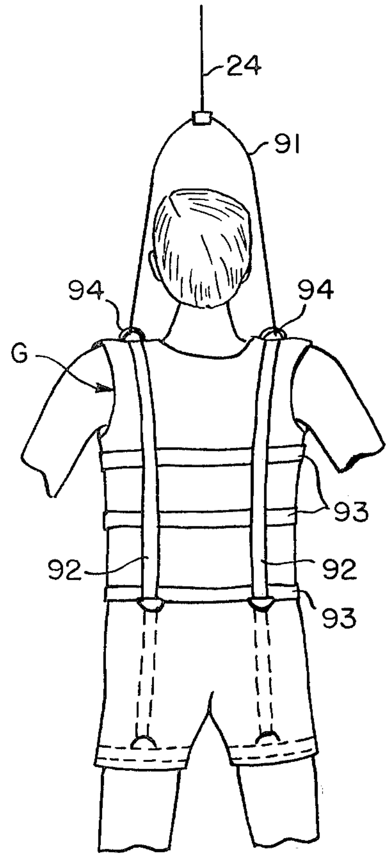
Figure 8:
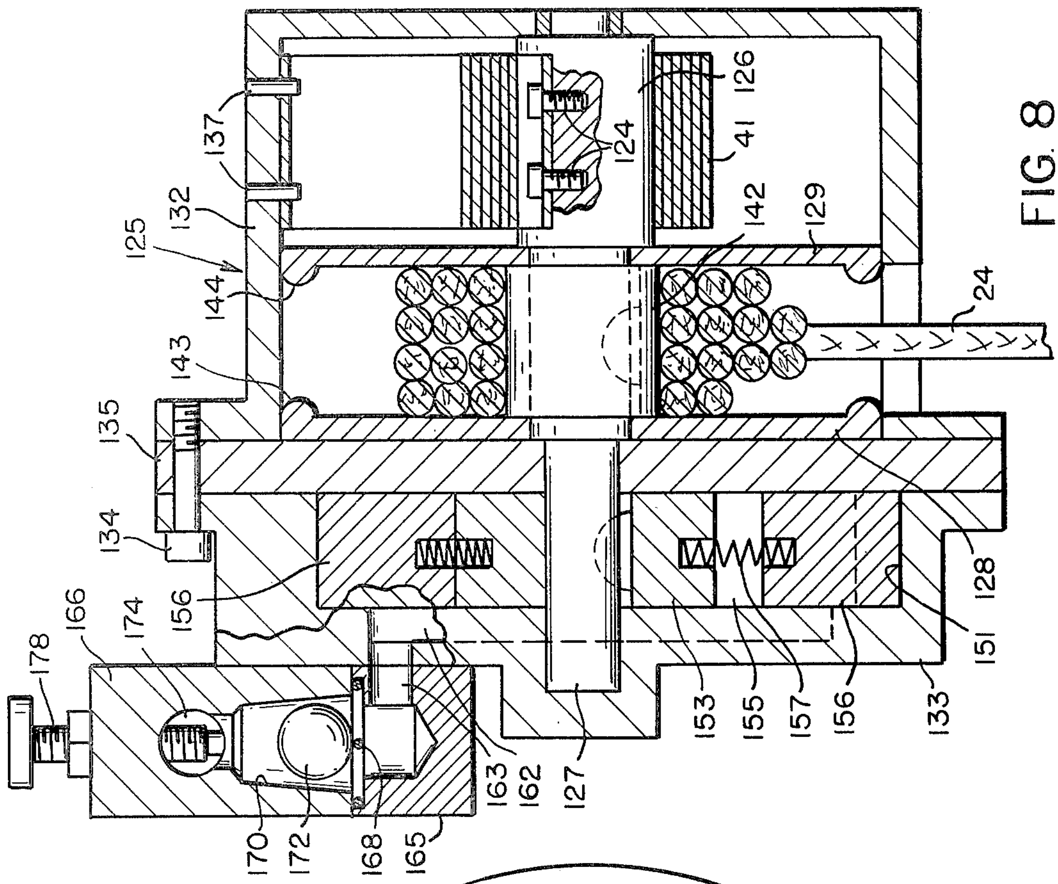
Figure 9:
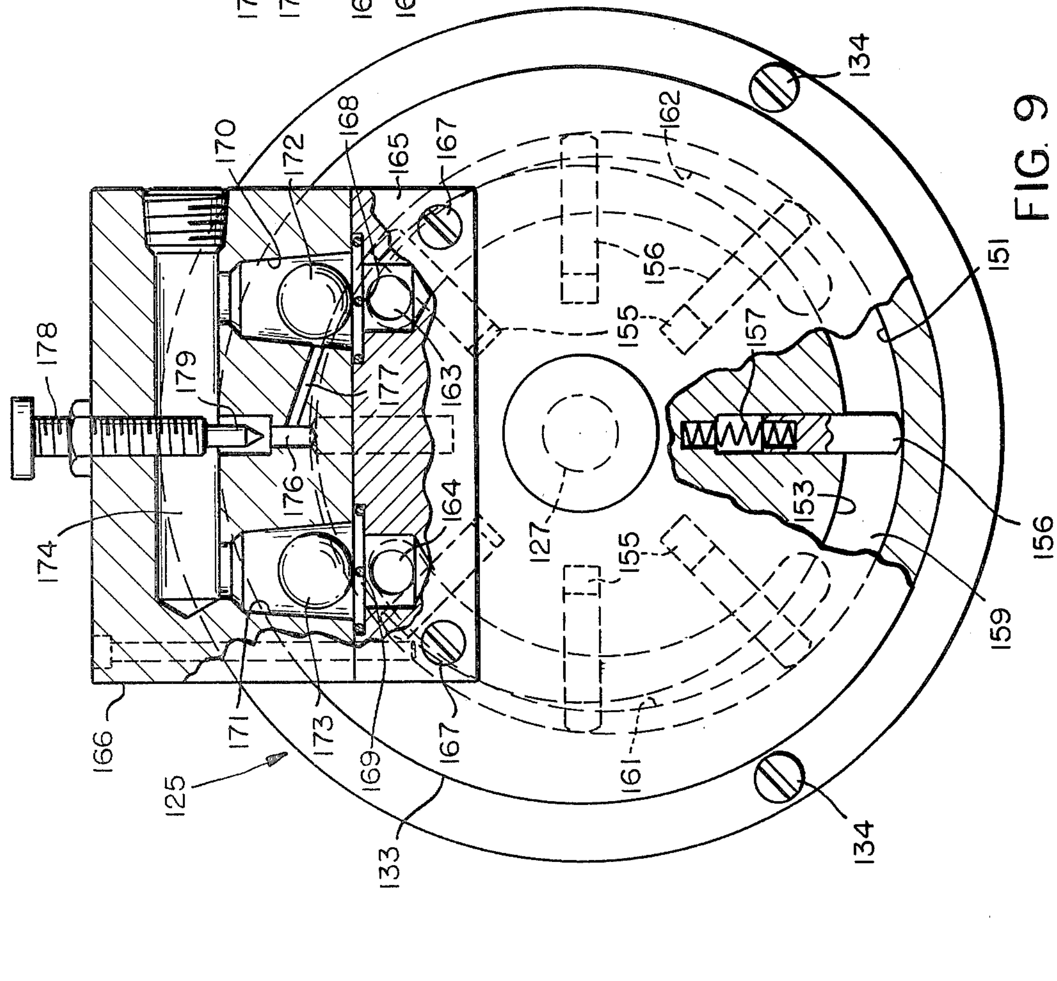

FIG. 5 is a bottom plan view of a closed loop overhead monorail practice track for use in learning and/or rehabilitation of a patient, and illustrating also side tracks projecting from the practice track;

FIG. 6 is a front elevational view of a modified form of a harness or restraint garment which is adapted to be employed in this invention;

FIG. 7 is a rear elevational view of this garment;

FIG. 8 is a fragmentary sectional view similar to FIG. 2, but showing a modified form of inertial reel which may be used with this invention; and FIG. 9 is an end elevational view of this modified reel as seen when looking at the left end thereof as shown in FIG. 8, and with portions thereof broken away and shown in section.

Referring now to the drawings by numerals of reference, and first to FIGS. 1 to 3, 21 and 22 denote a pair of hooked-shaped "shepherd staff" supporting members which form part of a safety harness supporting system made according to one embodiment of this invention. Members 21 and 22 are fixed at their upper ends to opposite ends of a yoke or supporting member 23, which is suspended by a retractable tether or cord 24 from an inertial reel, which is denoted generally by numeral 25 in FIGS. 2 and 3, and which is enclosed in a casing or housing 26 adjacent the ceiling C of a hospital room or the like. The upper end of cord 24 is wound about a shaft 27, which forms part of reel 25, and between a pair of disc-shaped members 28 and 29 which are fixed coaxially to shaft 27 approximately medially of its ends. Opposite ends of shaft 27 are rotatably journaled in a pair of annular bearings 31, one of which is fixed in a central opening in the closed end of a generally cupped-shaped drum housing or casing 33, and the other of which is fixed in the closed end of a similarly shaped but smaller housing 35. Housing 35 has around its open end an external, circumferential flange 36 that is releasably fastened by screws 37, or the like, to the open end of the housing 33 coaxially thereof.

Figure 3:
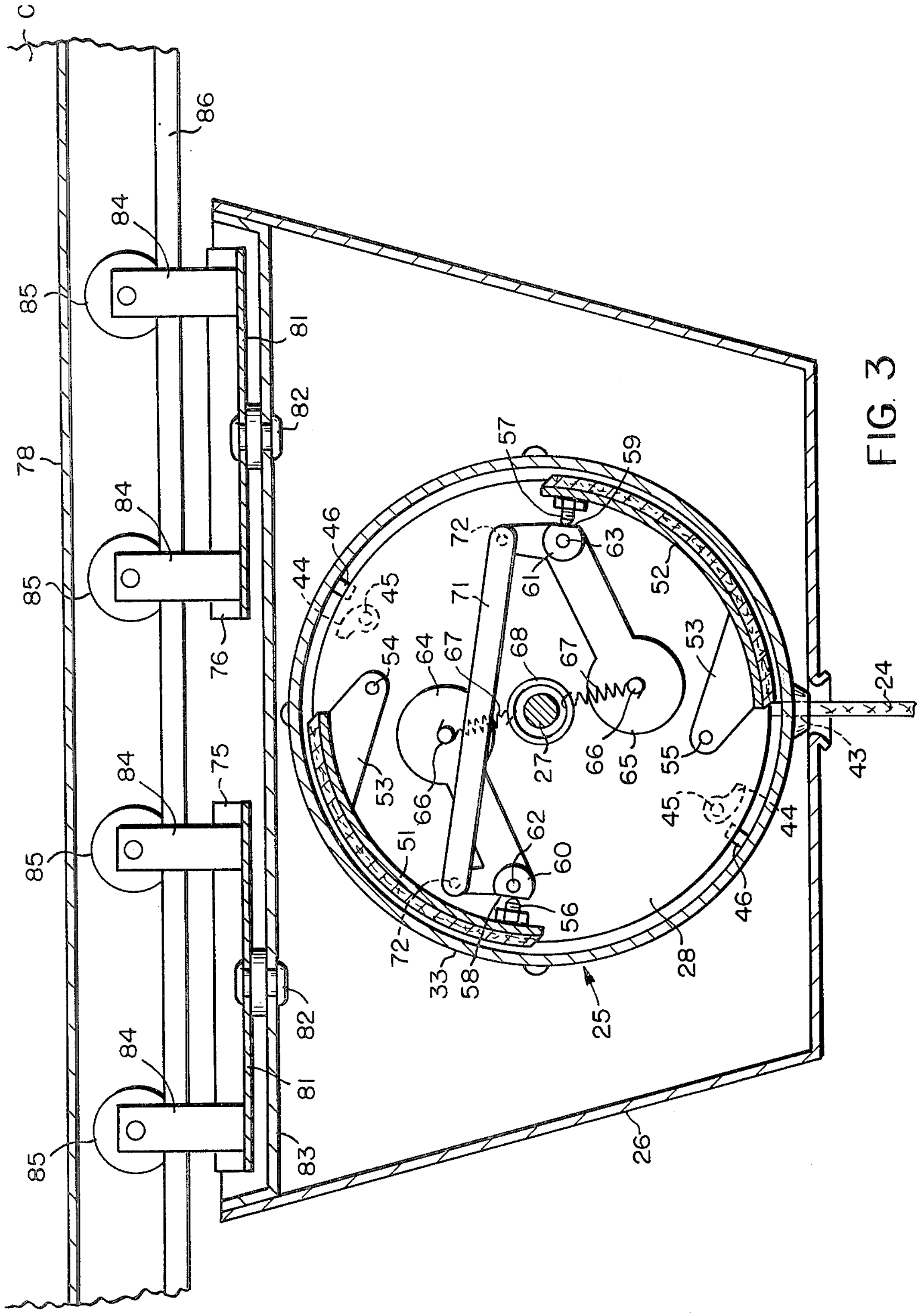
FIG. 3 is a fragmentary sectional view on the same scale and taken along the line 3—3 in FIG. 2 looking in the direction of the arrows.

Mounted in the casing 35 to surround one end of the shaft 27 (the right end as shown in FIG. 2) is a flat, coiled torsion spring 41, one end of which is fixed to the shaft 27, and the other of which is secured to the annular wall of casing 35, thereby resiliently to resist the rotation of the shaft 27 in one direction, for example clockwise about its axis as shown in FIG. 3. For this purpose the right end of shaft 27 may have a radial or diametral flat formed thereon against which one end of the spring 41 may be secured.

The cord 24 is fixed at one end to the shaft 27 and extends at its other end downwardly through an opening 43 formed in the annular wall of casing 33 and housing 26. The retraction of the cord back into the casing 33 is limited by a pair of conventional pawls 44, each of which is pivotally mounted at one end on one of a pair of pins 45 which project from one side of disc 29 (the right side as shown in FIG. 2) adjacent diametrally opposite sides thereof. The free ends of the pawls 44 are normally held in conventional manner by light torsion springs (not illustrated) in the positions shown in FIG. 3, so that their free ends are positioned radially inwardly from a pair of pins or stops 46, which project radially inwardly from the inner peripheral surface of casing 33 adjacent its open end, and at diametrally opposite sides thereof. When the cord 24 is retracted suddenly upwardly by the spring 41, the centrifugal force causes the spring-loaded pawls 44 to rotate outwardly to engage the free ends thereof with the pins 46, thus to prevent further retraction of the cord 24. The pawls 44 are mounted for limited pivotal movement about the pins 45, so that when they engage the stop pins 46 further rotation of the disc 29, and hence disc 28 and the shaft 27, is halted until such time that the cord 24 is again drawn downwardly or outwardly from the casing 33 far enough to permit the spring-loaded pawls to return to their inoperative positions as shown in FIG. 3.

Withdrawal of the cord 24 outwardly from the casing 33, so as to cause it to unwind from the shaft 27, is controlled by an inertial mechanism comprising a pair of arcuate brake shoes 51 and 52, each of which is mounted at one end by a bracket 53 to pivot about one of a pair of pins 54 and 55, respectively, which project from the outer surface of disc 28 adjacent diametrally opposite sides thereof. Adjustably threaded into the opposite ends of brake shoes 51 and 52, and projecting radially inwardly therefrom are two externally threaded studs 56 and 57, respectively. These studs engage flat camming surfaces 58 and 59 (FIG. 3) that are formed on the hubs of two, angular levers 60 and 61, which are mounted intermediate their ends by their respective hub portions to pivot about a pair of pins 62 and 63 which project from the face of disc 28 adjacent the free ends of the brake shoes 51 and 52. Each of the levers 60 and 61 has formed on one end thereof an enlarged, circular head portion 64 and 65, respectively. A pin 66, which projects axially from each head portion 64 and 65 at the side thereof remote from disc 28, is connected by a spring 67 to a ring 68, which surrounds shaft 27. The ring 68 has an inner diameter larger than that of the outer diameter of shaft 27, so that the ring 68 normally is disposed in radially spaced relation to shaft 27.

The opposite ends of levers 60 and 61 (the ends remote from portions 64 and 65) are interconnected by a rigid link 71, opposite ends of which are pivotally connected to pins 72, that project from the head portions 64 and 65 of the levers. Link 71 causes the pivotal motion of the arms 60 and 61 about pins 62 and 63 to be transmitted from one to the other, as noted in greater detail hereinafter. From an examination of FIG. 3 it will be noted that when these arms are pivoted from the positions shown in the drawings, the flat surfaces 58 and 59 thereon will bear against the studs 56 and 67 to pivot the brake shoes 51 and 52 into frictional engagement with the inner peripheral surface of casing 33. Normally the springs 67 hold the levers 60 and 61 in the positions shown in FIG. 3, so that shoes 51 and 52 are not held in frictional engagement with casing 33.

Figure 1:
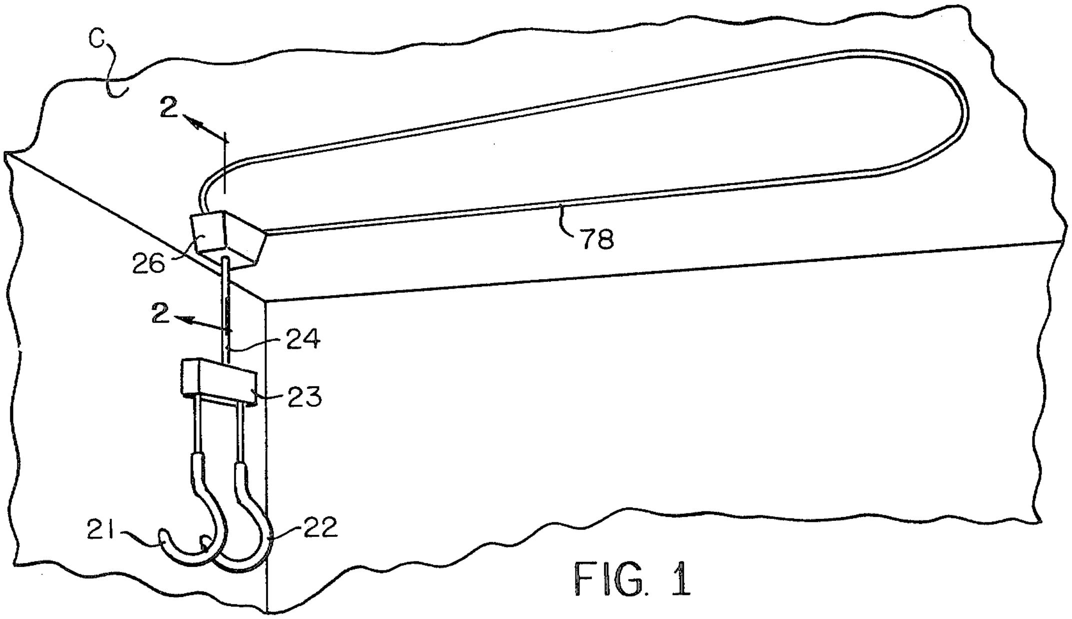

The casing 26, which contains reel 25, is suspended by a pair of wheeled tracks 75 and 76 from a hollow rail 78, which is mounted in a recess in the ceiling C to support the harness mechanism for movement in, for example, a closed loop as shown in FIG. 1. Each truck 75 and 76 comprises a base plate 81, which is riveted or otherwise secured as at 82 to the rigid, upper wall 83 of casing 26. Each of a pair of spaced posts 84, which project upwardly from the base plate 81 of each truck, carries on its upper end a pair of spaced, coaxial rollers 85, which have rolling engagement on a pair of spaced, parallel flanges 86, which are formed on the underside of rail 78 approximately coplaner with the surface of the ceiling C.

In use the harness mechanism can be moved by its trucks 75 and 76 to a position in which its supporting members 21 and 22 will register approximately with the shoulders or underarms of a patient P, who may be seated, for example on a chair S or the like as denoted schematically in FIG. 4A. The patient may then place the hook-shaped members 21 and 22 beneath his or her arm pits, and then rise from the chair S, at which time the spring 41 in reel 25 will cause the cord 24 to be retracted upwardly into the reel. The patient may then walk in a direction beneath and parallel to the ceiling track 78, during which movement the tensioned cord 24 will keep the members 21 and 22 engaged snuggly beneath the arm pits of the patient (FIG. 4B).

If while a patient is walking he or she should suddenly stumble toward the lowered position, as shown by broken lines in FIG. 4C, the sudden withdrawl of the cord 24 from the reel 25 will cause the enlarged head portions 64 and 65 of levers 60 and 61 to be swung by centrifugal forces radially outwardly away from the axial center line of the shaft 27. This outward movement of the head portions 64 and 65 against the resistance of springs 67 will cause the camming surfaces 58 and 59 on the hub portions of the levers to force the studs 56 and 57 radially outwardly, thereby causing the engagement of the brake shoes 51 and 52 with the inner peripheral surface of the stationary casing 33, and thus braking the fall of the patient P. Obviously the greater the rate at which the cord 24 is withdrawn from the reel 25, the greater will be the braking force exerted by the brake shoes 51 and 52 against the inner surface of the drum housing 33; and this braking force can be adjusted by rotating the studs 56 and 57 into desired positions relative to the associated camming surfaces 58, 59 on the hubs of the levers 60 and 61. In any event, the braking force created by shoes 51 and 52 will prevent the patient from falling too rapidly to the floor. Instead, the patient will be lowered gently to the floor.

The outward movement of the head portions 64 and 65 of the levers is resisted by the springs 67, so that when the rate of withdrawl of the cord 24 decreases, the springs will tend to return the levers to the positions illustrated in FIG. 3, so that the braking effect on the shoes 51 and 52 will be reduced proportionately. If, however, the cord 24 is suddenly retracted quickly upwardly into the reel 25, as for example upon the sudden release of the members 21 and 22, the centrifugal force imparted to the pawls 44 will cause them to rotate their free ends outwardly into engagement with the stationary stops 46 on casing 33, thus preventing further retraction of the cord until it is subsequently withdrawn at least slightly, to enable the pawls to disengage from stops 46 as noted previously.

The purpose of the link 71, which interconnects the levers 60 and 61, is to compensate for any gravitational forces which otherwise would tend to apply the brake shoes when the shaft 27 is not rotating. For example gravity tends to urge the head portions 64 and 65 of the levers downwardly in FIG. 3, thus tending to actuate shoes 51 and 52. These gravitational forces will have different potential effects depending upon the angular position of disc 28. The effects of these gravitational forces on portions 64 and 65 of the levers by the link 71, thus balancing out the gravitational forces and tending to cause the ring 68 to remain in radially spaced coaxial relation to the shaft 27.

FIG. 5 denotes schematically the ceiling rail 78 as seen in plan, and in combination with at least two different spur tracks 78-1 and 78-2, which communicate with the rail 78, and which would enable a patient using the harness mechanism in FIGS. 1 to 3 to move at his or her option either around the track 78, or off this track onto one of the spur tracks. The spur tracks could lead, for example, to another room or to another corridor in a hospital or the like.

FIGS. 6 and 7 illustrate a modified form of harness mechanism which can be employed in this invention in place of the hook-shaped members 21 and 22. In this embodiment the cord 24 is attached to the upper end of an inverted generally V-shaped yoke member 91, which is made of a rigid, polymeric-covered metal, polymer or segmented materials, to assure that it will not foul or become entangled on the user. The primary structure of the restraint garment can be in the form of a vest, leotard, or separate, adjustable harness. It can be fabricated from such materials as quilted nylon for strength and warmth, non-stretch polyester which provides necessary strength but less warmth, or as alternates, cotton, canvas or poplin with or without perferations depending upon the condition of the patient or user and the ambient temperature.

In the embodiment illustrated in FIGS. 6 and 7, the garment, which is denoted generally the the letter G, has an upper portion in the form of a vest and a lower protion in the form of a pair of shorts, which may or may not be integral with the vest portion. In one embodiment the vertical and horizontal straps 92 and 93, respectively, are stitched or otherwise secured to the vest portion of the garment, and may be made of $\frac{3}{4}$ inch reinforced cotton. A metal ring 94 is located in the shoulder portion of each vertical strap 92 for attachment by releasable coupling means of any conventional variety to one of the lower ends of the member 91. Additional straps may be employed in the leg areas of the garment as shown by broken lines in FIGS. 6 and 7, if desired. All strap closures and vest overlap sections and any other closure points of the garment and straps can be effected by the use of heavy duty zippers with positive locking mechanisms to prevent the user from removing the garment, if this feature is required; or "Velcro" tape closures can be used to take maximum advantage of their very high sheer strength and fully to utilize the quick-donning, easily removable aspects afforded by such closures. Moreover, although it has been suggested that the straps 92 and 93 be stitched to the garment itself, it is within the scope of this invention to employ the straps alone, placed over or under a patient's clothing, and with the straps being interconnected to each other through the use of "Velcro" tape closures, or the like. Referring now to FIGS. 8 and 9, 125 denotes generally another type of inertial reel which could be employed in this invention in place of reel 25. In this embodiment, wherein like numerals are employed to denote elements similar to those employed in the first embodiment, 127 denotes the reel shaft, which is rotatably journaled at opposite ends in the closed ends of generally cup-shaped housings 132 and 133, the open ends of which are secured by bolts 134, or the like, to opposite sides of a circular spacer plate 135. The shaft 127 extends rotatably through a central opening in the plate 135, and adjacent its right end as shown in FIG. 8 has thereon an enlarged-diameter portion 126, to which one end of a conventional, flat torsion spring 41 is secured by bolts 124. The opposite ends of spring 41 is secured as at 137 to the inner peripheral surface of the casing 132 adjacent its closed ends, thereby normally to urge shaft 127 to rotate in one direction.

A cord 24 is secured at one end to a sleeve 142, which is keyed to the shaft 127 between a pair of axially spaced discs or circular plates 128 and 129, which are also fastened to shaft 127 to rotate therewith in casing 132 between the plate 135 and the enlarged, diameter end 126 of the shaft. The axial space between the plates 128 and 129 is greater than the diameter of the cord 24, so that when shaft 127 is rotated in a wind-up direction, cord 24 tends to travel or wind axially back and forth on the sleeve 142 as the cord is would thereon. Annular bosses 143 and 144 formed on the confronting surfces of the disc at 128 and 129, respectively, are engageable with the cord 24 to reverse its travel each time it has traveled from one end to the other of the axial space between the discs, thereby causing the cord to wind evenly in the reel.

At its end remote from spring 41 the shaft 127 extends coaxially into the casing 133 toward the closed end thereof, and eccentrically with respect to a circular opening or counterbore 151, which is formed in the open end of casing 133 with its axis slightly offset from the axial center line of the casing. Keyed to shaft 127 for rotation thereby in the recess 151, and coaxially of casing 133, and eccentrically of the center line of the latter, is a circular pump rotor 153. Rotor 153 has a diameter slightly less than that of the counterbore 151, and has opposed, plane surfaces which rotate in closely spaced, confronting relation to one side of the spacer plate 135, and to the closed end of casing 133, respectively. At equiangularly spaced points around its periphery, the rotor 153 has therein radial slots or recesses 155 in each of which a generally rectangular pump vane 156 is mounted for snug, sliding movement radially of the rotor axis. Each vane 156 is urged radially outwardly in its associated recess 155 by a compression spring 157, opposite ends of which seat in registering recesses formed in the bottom of the associated vane 156, and the inner end or bottom of the associated slot 155. The springs 157 thus maintain the outer ends of the pump vanes 156 in resilient sliding engagement with the annular wall or surface of the recess 151 in the casing 133.

The diameter of the rotor 153 is such that during its rotation in the eccentrically disposed recess 151, the peripheral surface of the rotor 153 has nearly tangential engagement with the annular surface of the eccentric 151 at the uppermost point on this surface as shown in FIGS. 8 and 9; while diametrally opposite this point, or at the lowermost point of the eccentric surface 151 as shown in FIGS. 8 and 9, the outer peripheral surface of the rotor 153 is spaced from the annular wall of recess 151, therefore forming a nearly crescent shaped passage 159 (FIG. 9) in chamber 151 beneath the lower half of rotor 153.

The closed end of casing 133 has in its inner surface a pair of arcuate, shallow recesses or grooves 161 and 162, which are formed adjacent diametrally opposite sides of the closed end of this casing. As shown more clearly in FIG. 9, grooves 161 and 162 communicate at their lower ends with passage 159, and at their upper ends through ports 163 and 164, respectively, with opposite ends of a valve housing 166, which is secured by screws 167 to the exterior of casing 133. The ports 163 and 164 are connected in the housing 166 through screen members 168 and 169 with the lower ends, respectively, of two, truncated-conical valve chambers 170 and 171. These chambers contain ball valves 172 and 173, respectively, and communicate at their upper ends with opposite ends of a horizontally disposed duct 174, which is formed in the upper end of housing 166.

Medially of its ends duct 174 is connected by a vertical port 176 with the upper end of an inclined bleed duct 177, the lower end of which opens on valve chamber 170. Adjustably threaded in a vertical bore in the upper end of housing 166 is the externally threaded shank of a throttling or needle valve 178, the lower end of which has formed thereon a pointed stem 179 which is adjustable into or out of the port 176 to control the rate of flow of fluid through the bleeder duct 177.

In the embodiment illustrated each of the screen members 168 and 169 comprises a pair of intersecting pins or crossarms, the ends of which are seated in a recess which houses an O-ring or similar seal. Each screen member functions to prevent the associated valve 172 or 173 from descending far enough in its chamber to seat and close off the associated port 163 or 164, whereby fluid may always travel at least to a limited extent in a reverse direction through members 168 and 169. Also the chambers 170 and 171 are shaped so that the respective ball valves are not forced upwardly far enough in their chambers to close off the associated end of duct 174 unless the rate of flow of fluid upwardly through chamber 170 or 171 exceeds a predetermined value. Even then, when valve 172 is in its uppermost, or closed position, the fluid can bypass the valve through the bleeder duct 177.

The grooves 161 and 162 are designed so that most of the upper portions thereof, as shown in FIG. 9, are covered by the confronting face of the rotor 153, and the confronting surfaces and the pump vanes 156 which reciporcate radially in the rotor during its rotation. Below the dimetral midpoint of the casing 133, however, the outer peripheral surface of the rotor 153 curves away from the confronting peripheral surface on the recess 151, and thus begins to form the passage 159, and to uncover the lower ends of the grooves 161 and 162 so that any hydraulic fluid therein is free to enter the passage 159 and the spaces between the pump vanes 156.

In use, a supply of hydraulic fluid is placed in the pump chamber to fill the passage 159, the grooves 161 and 162, and the ducts in the valve housing 166 which are in communication with the ports 163 and 164. When the cord 24 is drawn downwardly out of the reel 125 against the resistance of torsion spring 41, the shaft 127 and the rotor 153 are rotated, for example counterclockwise in FIG. 9 relative to the casing 133. During this rotation the vanes 156 cause the hydraulic fluid in the passage 159 in casing 133 also to be swept counterclockwise or toward the groove 162. If this withdrawal rate of cord 24 is below the rate for which valve 172 is designed to close, the hydraulic fluid will be forced out through the port 163, through the screen member 168 and valve chamber 170 and around valve 172 to the duct 174 in the valve housing 166, and then back through chamber 171, screen member 169 and the port 164 into groove 161. The fluid is then reintroduced into the spaces between the pump vanes 153 in the passage 159 during continued rotation of shaft 127.

The greater the speed at which the shaft 127 is rotated clockwise, the greater will be the resistance to rotation caused by the hydraulic fluid. Moreover, whenever the cord 24 is withdrawn too rapidly, as for example when the attached patient stumbles and begins to fall, the sudden surge of fluid into the bottom of chamber 170 will cause valve 172 to rise to its uppermost position to cut off any further flow of fluid into the right end of duct 174 as illustrated in FIG. 9. Then, any further withdrawl of the cord 24 is controlled by the slower rate of flow of fluid through the bleeder duct 177 and past the pointed end of the adjustable needle valve 178. Obviously this valve can be set to cause a patient to be lowered slowly to the floor after his or her initial stumble has caused valve 172 to be shifted to its closed position.

When the cord 24 is released and allowed to be returned by spring 41 into the reel 125, the fluid in the pump housing flows in the opposite direction from port 164, through the valve casing 166 to port 163. If this return is sudden, valve 173 will be forced by the sudden flow of fluid to its upper, closed position, where it will remain momentarily to stop retraction of the cord momentarily. Then valve 173 will settle in chamber 171 and allow the cord to complete its retraction.

Although not shown in FIGS. 8 and 9, it is to be understood that, if desired, locking pawls such as those denoted at 44 in FIGS. 2 and 3 could be mounted on disc 128 or 129 for engagement with stop lugs or detents on casing 132 to lock shaft 127 against further rotation in a cord retracting direction, whenever the tension in cord 24 is suddenly released.

From the foregoing, it will be apparent that the instant invention provides relatively simple and effective means for preventing accidents and falls and consequent injuries to ambulatory patients, (and for that matter certain non-ambulatory) elderly people, and in general anyone ill enough to require some form of restraint to avoid accidental falls. With the herein disclosed invention such patients can be allowed to walk unattended, and without concern for their safety. The novel safety apparatus as disclosed herein may utilize the hooked-shaped members of the first embodiment to enable a person readily to engage or disengage the safety apparatus; while for more serious cases, the body encircling harness or garment shown in FIGS. 6 and 7 can be employed in conjunction with the rigid yoke member 23 or the semirigid yoke member 91 for attaching the patient's harness to the inertial reel mechanism.

The inertial reel mechanisms as disclosed herein have the advantage that, in those cases where they are movable along a ceiling rail, or the like, they are capable of being moved by the patient himself or herself, during the normal travel of the patient in whatever path is afforded by the overhead track 78. During this travel, of course, the associated reel 25 or 125 will function to restrain the associated patient from collapsing suddenly and injurying himself or herself. The reel mechanisms may be either of the mechanical variety as shown in FIGS. 2 and 3, or of the hydraulic variety as shown in FIGS. 8 and 9. In either case, any sudden withdrawl of the cord 24 will immediately apply a braking force which will gently lower the attached patient to the ground, thereby preventing any sudden jarring or jolting which might cause undesirable strains in the patient's body. Each of the reel mechanisms, as noted above, can be adjusted to control the rate of descent of the patient, or the unwinding of the cord or tether 24 from the associated reel. Moreover, any undesirable sudden retraction of the cord 24 is prevented either thorugh the use of safety pawls of the type shown in FIGS. 2 and 3, or as a result of the hydraulic system as incorporated in the embodiment shown in FIGS. 8 and 9, or through a combination of these features.

Among the numerous advantages afforded by this novel apparatus is the fact that it can be incorporated with little or no effort into existing institutions which care for the elderly. While in the embodiments illustrated all the track 78 is shown to be embedded in the ceiling of a room, it will be readily apparent to one skilled in the art that the track could be fastened onto the surface of an existing ceiling, rather than being embedded therein, therefore simplifying the installation of the overall apparatus. This apparatus would be particularly suitable for use in physiotherapy allowing a number of patients to engage in therapy at the same time, and without requiring the presence of an attendant at all times to prevent accidental falls and injuries to the patients. The desired course a patient is to take could be marked on the floor of the rooms or the halls, and the overhead guide mechanism or track 78 of the system can be located close enough to one wall to provide positive identification points for persons with impaired vision to verify their positions by touch.

Still another advantage of this system is that the inertial reels disclosed herein allow reasonable freedom of movement of very slow velocities in a downward or tether withdrawal direction, while keeping the tether without slack—i.e., taut but without objectionable upward force being exerted against the patient. The constant upward force, which is exerted on the patient by the tether, helps to instill confidence in a patient and increase his or her peace of mind. The subject using the apparatus may arise, at which time the inertial reel automatically winds up the tether so as continuously to maintain tautness therein. The patient using the equipment may sit, lie, or otherwise lower his or her body at a slow velocity with virtual ease as long as the velocity, or rate change of velocity, does not exceed the inertial reel's threshold level of change. Once this occurs, the reel brakes immediately and after a slight pause allows the patient or subject slowly to be lowered onto the bed, chair, or floor without achieving a velocity sufficient to allow injury.

The length of the tether or cord 24, of course, is sized to allow the patient to maintain light contact with the floor, again with the tether remaining in a taut condition without slack, and without any significant upward force. The inertial reel itself, as desired, may be anchored in a fixed position above the bed, locked into position on an overhead monorail, or may be allowed to move along the monorail or track 78 depending on the desired options. Moreover, the reel could be fixed to a frame formed over the top of a conventional walker so as to be movable with the walker, and with its tether attachable to the person using the walker. Not only do the reels disclosed herein allow slow and gentle lowering of the patient to the floor or bed, thereby avoiding a fall and potential injury, but they also avoid the undesirable condition of hanging or suspending the patient at the point where the fall is initially interrupted.

While it has been suggested that the track 78 can be modified as desired to allow spur tracks leading to positions in different rooms or corridors of a building, or the like, it will be apparent that the transfer from the main track 78 to a spur or branching track will be effected by the use of any conventional switching means currently known or under development and available for performing such transfers. Moreover, while this system is particularly suited for use in hospitals and the like, it will be apparent that it could be used in other environments, including personal homes or residences where the need for such a restraint system arises.

While this invention has been described in connection with several embodiments thereof, it will be apparent that it is capable of still further modification, and that this application is intended to cover any such modifications as may fall within the scope of one skilled in the art or the appended claims.

Having thus described our invention, what we claim is:

1. A safety restraint system for ambulatory patients comprising an overhead track, an inertial reel mounted for movement horizontally on said track in a predetermined path, a retractable cord extending downwardly from said reel, and harness means on the lower end of said cord for releasably connecting said cord to an ambulatory patient, or the like, whereby upon movement of said patient along a path parallel to said overhead track, said reel is caused to travel on said track along said predetermined path, said reel including first means resiliently resisting withdrawal of said cord from said reel, and second means for automatically increasing the resistance to withdrawal of said cord from said reel, when the rate of withdrawal of the cord exceeds a predetermined value.

2. A safety restraint system as defined in claim 1, wherein said first means is operable to retract said cord back onto said reel upon release of said lower end of the cord, and said reel further includes means for automatically stopping the retraction of said cord onto said reel when the rate of retraction of said cord exceeds a predetermined value.

3. A safety restraint system as defined in claim 1, wherein said second means comprises a braking member movable into and out of sliding, frictional contact with a stationary surface on said reel, a rotatable shaft on said reel connected to said cord for rotation thereby in one direction upon withdrawal of the cord from said reel, and means interposed between said shaft and said braking member and operative, when the rotation of said shaft exceeds a predetermined value, to urge said braking member into frictional contact with said stationary surface.

4. A safety restraint system as defined in claim 3, wherein the last-named means comprises an operating member, connected to said shaft for rotation therewith and responsive to centrifugal forces generated by the last-named rotation to urge said braking member into engagement with said stationary surface with a force which is proportional to the rate at which the rotation of said shaft exceeds said predetermined value in said one direction.

5. A safety restraint system as defined in claim 4, wherein there are two of said braking members, and two of said operating members are rotatable with said shaft, and said two operating members are interconnected for movement in unison between braking positions in which they urge said braking members into contact with said stationary surface, and released positions in which said braking members are free to disengage said surface.

6. A safety restraint system as defined in claim 1, wherein said second means comprises a hydraulic pump housing a rotatable shaft on said reel and connected to said cord for rotation thereby in one direction upon withdrawal of the cord from said reel an impeller mounted in said pump housing and rotatable by said shaft to pump fluid from one port to another in said housing during rotation of said shaft in said one direction, and valve means interposed between said ports and operative, when the rotation of said shaft in said one direction exceeds a predetermined value, to increase the resistance to the flow of fluid through said housing from said one port to the other.

7. A safety restraint system as defined in claim 6, wherein said impeller comprises a generally disc-shaped rotor mounted to rotate in a circular chamber in said pump housing, and having at least a portion of its periphery spaced from the peripheral wall of said chamber, a plurality of pump vanes are mounted for radial sliding movement in axially spaced recesses in the periphery of said rotor, and with the outer ends of said vanes disposed in sliding engagement with the surrounding, peripheral wall of said chamber, and means for conveying hydraulic fluid into the passage formed between the spaced peripheral portion of said rotor and chamber for conveyance by said vanes from said one to the other port in said housing during rotation of said shaft in said one direction.

8. A safety restraint system as defined in claim 7, wherein said rotor has a diameter smaller than that of said chamber and is mounted therein with its axis extending parallel to and offset from the axis of said chamber.

9. A safety restraint system as defined in claim 1, wherein said harness means comprises a pair of rigid, hook-shaped members suspended from said cord and releasably engageable beneath the arm pits of said patient.

10. A safety restraint system as defined in claim 1, wherein said harness means comprises a vest-like garment disposed to be worn by said patient, and having thereon a plurality of spaced straps certain of which have thereon means for releasably attaching said certain straps to said cord.

11. Safety restraint apparatus for preventing injury to a hospital patient, or the like, resulting from sudden stumbling or collapse of the patient, comprising a housing mounted on an overhead frame, a shaft rotatably mounted on said housing, a flexible tether attached at one end to said shaft to be wound thereon upon rotation of said shaft in one direction, and to unwind from said shaft upon rotation thereof in the opposite direction, harness means attached to the opposite end of said tether releasably to be connected to a patient, resilient means urging said shaft to rotate in said one direction and resisting rotation thereof in said opposite direction, and operative to maintain said tether in a taut, unslackened condition, when said harness means is connected to a patient, and inertial means interposed between said shaft and said housing and operative, when the rate of rotation of said shaft in said opposite direction exceeds a predetermined value, progressively to increase the resistance to the rotation of said shaft in said opposite direction in proportion to the excess of the last-named rate above said predetermined value.

12. Safety restraint apparatus as defined in claim 11, wherein said overhead frame is a rail mounted on the ceiling of a room, and means is provided for mounting said housing for movement by said patients along said rail.

13. Safety restraint apparatus as defined in claim 11, wherein said harness means comprises a garment disposed to be worn by said patient, a yoke member attached to said opposite end of said tether and having a pair of spaced ends disposed to register with the shoulders of a patient, and means for releasably attaching said spaced ends of said yoke member to said garment adjacent the shoulders of said patient.

14. Safety restraint apparatus as defined in claim 11, wherein said harness means comprises a pair of support members secured to said opposite end of said tether and having thereon hook-shaped portions engageable under the arm pits of said patient.

* * * * *